(12) United States Patent
Neubert

(10) Patent No.: US 6,634,237 B2
(45) Date of Patent: Oct. 21, 2003

(54) COLLECTION RESERVOIR FOR USE WITH FLOW METER CONTROL SYSTEM

(75) Inventor: William J. Neubert, Ballwin, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/997,901

(22) Filed: Nov. 30, 2001

(65) Prior Publication Data

US 2003/0101826 A1 Jun. 5, 2003

(51) Int. Cl.[7] ................................................. G01F 1/58
(52) U.S. Cl. ...................................... 73/861.12; 604/22
(58) Field of Search ........................ 73/861.12, 861.21, 73/861.18; 128/205, 205.29, 205.27; 604/22; 434/262; 606/48, 40

(56) References Cited

U.S. PATENT DOCUMENTS

| | | | | |
|---|---|---|---|---|
| 3,773,037 A | * | 11/1973 | Kolin | 600/505 |
| 3,838,683 A | * | 10/1974 | Kolin | 104/114 |
| 4,770,654 A | * | 9/1988 | Rogers et al. | 604/22 |
| 5,139,458 A | * | 8/1992 | Koukal et al. | 454/147 |
| 5,647,871 A | * | 7/1997 | Levine et al. | 606/45 |
| 5,669,907 A | * | 9/1997 | Platt et al. | 606/34 |
| 5,836,909 A | * | 11/1998 | Cosmescu | 604/35 |
| 5,969,236 A | * | 10/1999 | Hirota et al. | 310/338 |

* cited by examiner

*Primary Examiner*—Edward Lefkowitz
*Assistant Examiner*—Jewel V. Thompson
(74) *Attorney, Agent, or Firm*—Michael L. Smith

(57) ABSTRACT

A collection reservoir 54 includes a rigid-walled cassette adapted for connection to aspiration tubing 50. The cassette also includes a pair of electrodes 36 positioned so that the electrodes are electrically connectable to a flow meter 34. In operation, the electrodes are exposed to the fluid and tissue being aspirated from the surgical site so that the flow meter indicates a flow rate of the fluid and tissue from the surgical site.

2 Claims, 1 Drawing Sheet

COLLECTION RESERVOIR FOR USE WITH FLOW METER CONTROL SYSTEM

BACKGROUND OF THE INVENTION

1. Field of the Invention

The present invention is related to sensing an aspiration flow rate in a surgical pump system. More particularly, the present invention is directed towards a flow meter and control system for use with surgical pump systems.

2. Description of Related Art

The flow and flow rate of tissue and fluids through an aspiration tube is of interest during operations, including ophthalmic operations. However, direct measurement of the flow rate is typically impractical. Flow rates are generally inferred for positive displacement pumps, e.g., flow-based pumps that are based on pump rotation or other in-direct periodic measurements, these pumps are also commonly referred to as peristaltic pumps. Flow rates for venturi-based pumps have generally not been measured nor has an indirect measurement been used.

Measurement of the surgical aspiration flow rate may be valuable in that it can provide for safe control of the ophthalmic surgical equipment. In most positive displacement-based systems, flow has been known to be inferred from the cycle frequency, i.e., the rotation rate, of the aspiration pump. However, this inference may be invalid in situations where there are varying pressure differentials within the pump system. The pressure variations may occur as a result of changes in the irrigation-fluid bottle height, changes in the viscosity of the aspirant, and changing occlusion conditions at the distal end of the aspiration tube. For known venturi-based aspiration systems no flow measurement has previously been feasible, nor can flow be accurately inferred from the vacuum level. This is because the actual flow rate varies with the viscosity of the aspirant and the occlusion state of the aspiration tube.

In the prior art, it is possible to measure the flow rate in the aspiration tube with a positive displacement or venturi-based system or any other type of pump system using traditional flow sensors. These traditional flow sensors include paddle-wheel, hot-wire, or other devices which are deflected in the presence of fluid flow. However, these devices become contaminated or closed by the aspirant and cannot be reused on a different patient, thereby making the use of such sensors expensive.

Therefore, it would be desirable to have a low-cost flow sensor that could be inexpensively incorporated into a disposable or reusable system to directly measure flow rate. Such a flow measurement can enable new modes of operation, particularly for vacuum-based systems. One such application is the emulation of a flow-based pump by a vacuum-based pump using an additional control loop.

DETAILED DESCRIPTION OF THE PREFERRED EMBODIMENT

Figure 1:
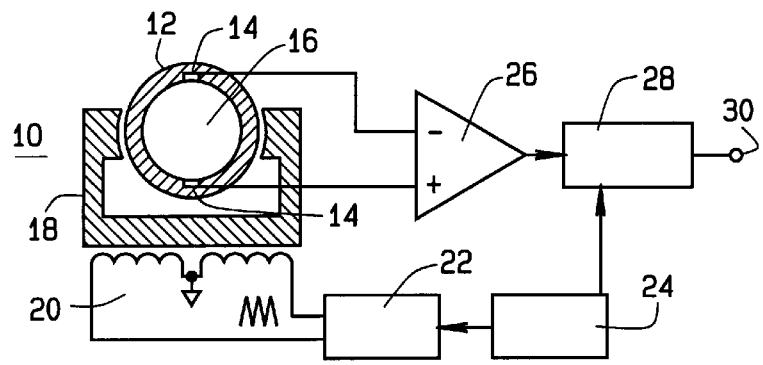
FIG. 1 is a prior art circuit diagram of a Hall-effect flow meter.

Hall-effect flow meters for sensing the flow of conductive fluids are known. Such a prior art Hall-effect flow meter is shown in FIG. 1. The flow meter 10 includes a conduit 12 including electrodes 14 that are in communication with the inner diameter of conduit 12 such that the electrodes are in contact with conductive fluids 16 flowing through conduit 12. A magnetic core 18 is placed around conduit 12 so as to induce an electromagnetic field perpendicular to a line-drawn through electrodes 14. Transformer 20 is connected to driver 22 and oscillator 24. Signals from electrodes 14 are amplified by amplifier 26, and the amplified signals are fed to synchronous demodulator 28. A signal representative of the flow rate of the conductive fluid 16 is outputted to node 30.

Ophthalmic surgical systems can be broadly categorized as flow-based or vacuum-based. Flow-based pump systems attempt to maintain a constant or controlled rate of flow within specific vacuum ranges. A feedback or control loop may be used to ensure the constancy of the drive system under differing loads conditions. An additional feedback control loop may exist between a vacuum sensor in the aspiration line in the motor, to limit the amount of vacuum in the aspiration tube.

Vacuum-based systems also have feedback control loops, where the signal from a vacuum sensor in the aspiration path is compared to the pre-set desired vacuum level. Error signals are then sent to a vacuum generator, such as a proportional value and venturi chamber, to increase or decrease the vacuum level.

In certain situations, the emulation of a flow-based pump system by a vacuum-based pump system may be desirable. Such emulation has not been practical before the present invention, because there has been no practical means to measure flow rate in the vacuum-based system.

Figure 3:
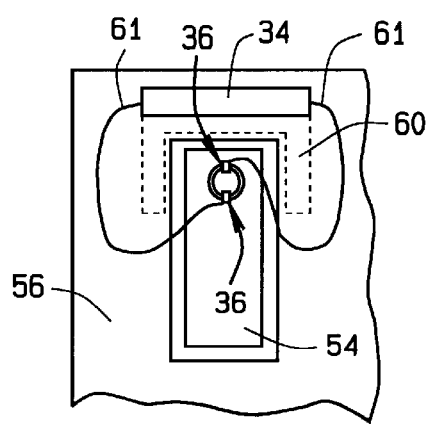
FIG. 3 is a front view of a surgical cassette inserted in a console in accordance with the present invention.
Figure 4:
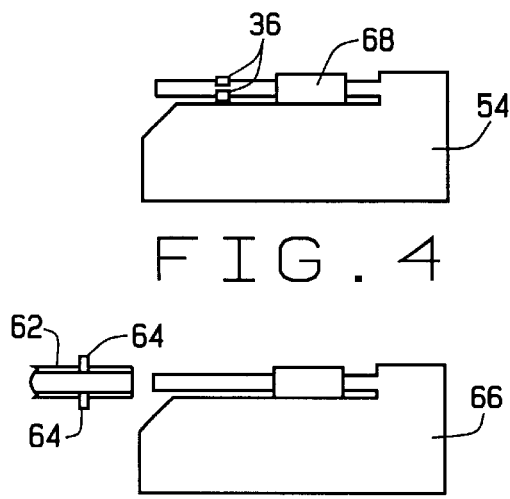
FIG. 4. is a surgical cassette in accordance with one aspect of the present invention.
Figure 5:
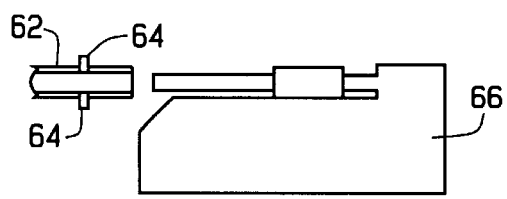
FIG. 5 is an illustration of an aspiration tube for connection to a surgical cassette in accordance with an alternative embodiment of the present invention.

The present invention solution for ophthalmic aspiration flow rate measurement preferably utilizes an isolated Hall-effect electromagnetic flow meter, such as described above in FIG. 1. The present invention, shown in FIG. 2, takes advantage of the fact that the saline solution commonly used in ophthalmic surgery is electrically conductive. Thus, a Hall-voltage can be induced across an aspiration tube if a magnetic field is applied. The flow meter 34 (preferably similar to the flow meter 10 of FIG. 1) in the ophthalmic surgical pump system 32 includes of a magnetic field source or electromagnetic magnet and meter 34 in use is connected to a disposable electrode assembly 36 (as shown in FIGS. 3–5). Control electronics assembly 38, preferably responds to the output of flow meter 34, to control a proportional value or venturi chamber (not shown) of a venturi pump 56 to emulate a peristaltic pump by maintaining a constant flow rate of fluids and tissues through path or tube 50. The preferred embodiment shows an aspiration tube 50, but the tube 50 could also be other pathways that allow fluids and tissues to be carried away from the surgical site.

Figure 2:
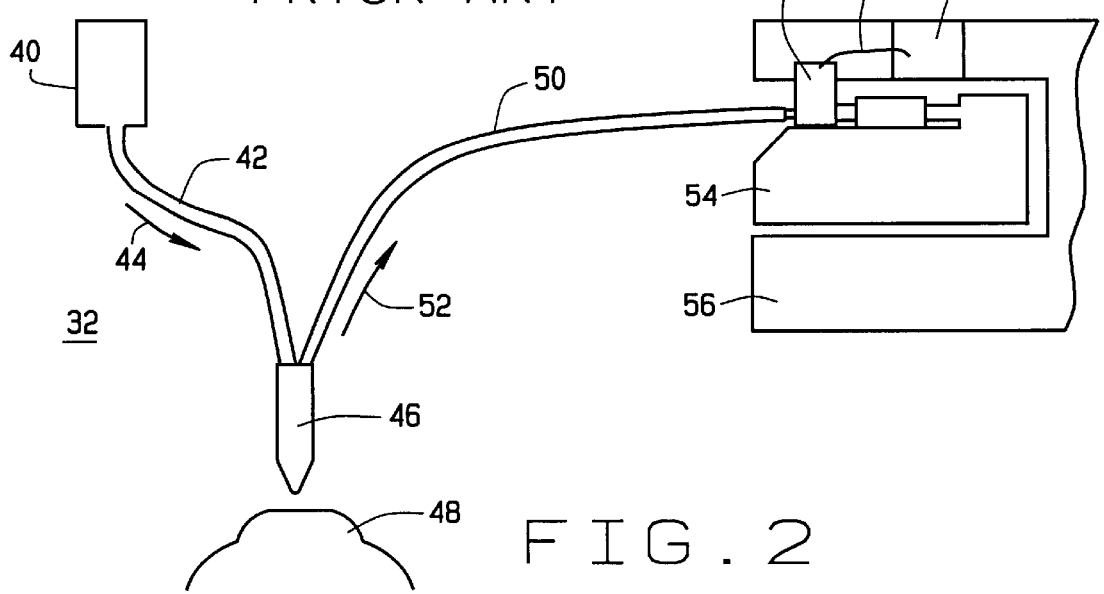
FIG. 2 is a partial cut-away view of a pump system in accordance with the present invention.

FIG. 2. further shows an irrigation-fluid bottle 40 connected to an irrigation line 42, with arrow 44 showing the direction of travel of the saline fluid into handpiece 46. Surgical handpiece 46 performs a surgical operation on eye 48. Fluids from bottle 40 and excised surgical tissue are aspirated from eye 48 through aspiration path 50 (which is preferably standard surgical tubing) in the direction shown by arrow 52. The aspirated fluid and tissue is received by collection reservoir 54 which is contained within pump 56 (preferably a venturi pump though a peristaltic or other pump may be used as well). The venturi pump is preferably the same pump sold with Bausch & Lomb's Millennium®

Ophthalmic Surgical System. Venturi pump 56 creates a vacuum level for aspirating fluid and tissue from the surgical site at eye 48 to the collection reservoir 54. The flow meter 34 is electrically connected (connection shown at 58) to control circuitry 38, as well as being electrically connected to one of the aspiration tubing 50 or the collection reservoir 54 as further described below. Control circuitry 38 is connected to the flow meter 34 and to venturi pump 56 for varying the vacuum level of the pump 56 and thereby maintaining a desired flow rate of the fluid and tissue being aspirated from the surgical site.

Preferably, collection reservoir 54 is a rigid-walled cassette so that the cassette will be operable and not collapse during operation when a vacuum level is applied by the venturi pump 56. Further collection reservoir 54 is similar to cassettes currently sold by Bausch & Lomb except as modified and described in this invention. Electrodes 36 are not visible in the view of FIG. 2 though may be seen in alternative embodiments in FIGS. 3–5.

FIG. 3 shows a partial front view of a venturi pump 56 including a collection reservoir 54 for use in surgical pump system 32. Collection reservoir 54 is preferably a rigid-walled cassette adapted for connection to the aspiration tubing 50 and receives fluid and tissue aspirated from a surgical site. Collection reservoir 54 also includes a pair of electrodes 36 positioned so that the electrodes are electrically connectable to flow meter 34. During operation, the electrodes 36 are exposed to the fluid and tissue such that the flow meter 34 shall indicate a flow rate of the fluid and tissue from the surgical site. Preferably, electrodes 36 are positioned so that, in operation, electrodes 36 align perpendicular to an electromagnet 60 thereby forming a Hall-effect flow meter. FIG. 4 shows a side elevation view of a collection reservoir 54 as described above. Electrodes 36 may be molded into the reservoir 54 or inserted by any other known method, but in any case, the electrodes should form a sufficient seal with reservoir 54 to prevent fluids from leaking.

FIG. 5 is an alternate embodiment of the present invention, wherein surgical tubing 62 is essentially the same as tube 50 except that tube 62 includes a pair of electrodes 64 for cooperation with electromagnet 60 and flow meter circuitry 34 and is shown to be connectable with a collection reservoir 66. Surgical tubing 62 carries fluid to or from a surgical site and includes a pair of electrodes positioned within the tubing such that the electrodes, in operation, are exposed to the fluids and wherein the electrodes are electrically connectable to a flow meter for indicating a flow rate of the fluids through the tubing. Preferably, the electrodes 64 are positioned so that, in operation the electrodes are perpendicular to an electromagnet, such as that shown in FIG. 3, to form a Hall-effect flow meter. Electrodes 64 may be molded into tubing 62 or may be press fit and should form a liquid tight seal with tubing 62.

The flow meter 34 provides a magnetic field required to produce the Hall-effect voltage. The magnetic driver can be constructed of a permanent or preferably an electromagnet. An electromagnet is preferred so that the magnetic field may be oscillated. Alternatively, the field may be oscillated by rotation of a fixed cylindrical magnet (not shown). In either configuration, an air gap is required so that the aspiration tube may be inserted within the magnetic field. The disposable electrodes 64 or 36 must be in contact with the aspirant. These electrodes may be molded into an aspiration tube 60 as shown in FIG. 5, into a cassette 54 as shown in 3 and 4, or into a reflux bulb 68 at low cost. It is also noted that a Hall-effect flow meter as described, can be connected to irrigation tubing 42 to provide an accurate flow rate of the saline solution into the eye.

The metal electrodes 36 or 60 are in contact with the aspirated saline solution resulting in an electrochemical reaction, such as corrosion, which, in turn, produces electrical signals. The use of an alternating magnetic field from the Hall-effect flow meter induces alternating voltages. The amplitude of this alternating field is then correlated to a flow rate. Electrochemical voltages not associated with the flow rate are filtered and eliminated easily because they are steady currents.

Thus, there has been shown an inventive flow meter for an ophthalmic surgical pump system. This flow meter could be used with flow-based pumps or vacuum-based pumps as described above.

Important application using the flow meter 34 in connection with the venturi-based pump system is the emulation of a positive displacement pump. The flow rate output of meter 34 can be used in a feedback control loop to adjust the vacuum level. This feedback control loop is preferably part of control circuitry 38. This control loop consists of measuring the flow rate with meter 34 and comparing that rate to the commanded flow rate. If the sense flow rate is lower than commanded, a vacuum generator level is increased to generate additional vacuum. This in turn increases the flow rate. Conversely, if the flow rate is too high, the vacuum generator level is decreased resulting in a decreased flow rate. In this way, using control system design the characteristics of a flow-based pump may be emulated using venturi pump 56. With or without a feedback control loop, it is preferred that the flow rate detected by flow meter 34 be displayed (not shown) by pump system 32.

An additional application of flow sensor 34 is occlusion detection. Essentially, occlusion detection is simply another flow rate detection scheme where the flow rate detected approaches zero (0) when tissue blocks the tip of a surgical device or the aspiration tube. When the flow rate approaches zero (0) dangerous conditions result such as overheating of the surgical device or occlusion of the aspiration pathway and quick detection of such a condition is highly desirable. Therefore, detection of a flow rate approaching zero (0) could be used to warn the user (audibly or visually) that the system has an occlusion or upon detection the aspiration could be slowed or stopped. As those skilled in the art will appreciate, the detection and warning of a flow rate need not be at zero (0), but could occur at some flow rate above zero (0), but where overheating may still be of concern.

Thus, there has been shown an inventive ophthalmic surgical pump system providing a low-cost aspirant flow meter. In addition, such a system may be used in other surgical pump systems, such as endoscopic pumps.

We claim:

1. A collection reservoir for use in a surgical pump system comprising:

a rigid-walled cassette adapted for connection to an aspiration tube and for receiving fluid and tissue aspirated from a surgical site; and a pair of electrodes molded into the cassette and positioned so that the electrodes are electrically connectable to a flow meter wherein the electrodes, in operation, are exposed to the fluid and tissue such that the flow meter indicates a flow rate of the fluid and tissue from the surgical site without the electrodes interfering with the flow of fluid and tissue through the cassette.

2. The reservoir of claim 1 wherein the electrodes are positioned so that, in operation, the electrodes align with an electromagnet thereby forming a Hall-Effect flow meter.

* * * * *